US 9,689,822 B2

(12) United States Patent
King et al.

(10) Patent No.: US 9,689,822 B2
(45) Date of Patent: Jun. 27, 2017

(54) CHARACTERIZATION OF DIELECTRIC MATERIALS

(71) Applicant: UT-Battelle LLC, Oak Ridge, TN (US)

(72) Inventors: Danny J. King, Ann Arbor, MI (US); Susan Babinec, Midland, MI (US); Patrick L. Hagans, Cleveland Heights, OH (US); Lonnie C. Maxey, Powell, TN (US); Edward A. Payzant, Oak Ridge, TN (US); Claus Daniel, Knoxville, TN (US); Adrian S. Sabau, Knoxville, TN (US); Ralph B. Dinwiddie, Knoxville, TN (US); Beth L. Armstrong, Oak Ridge, TN (US); Jane Y. Howe, Oak Ridge, TN (US); David L. Wood, III, Knoxville, TN (US); Nicole S. Nembhard, Richmond, IN (US)

(73) Assignee: UT-Battelle, LLC, Oak Ridge, TN (US)

( * ) Notice: Subject to any disclaimer, the term of this patent is extended or adjusted under 35 U.S.C. 154(b) by 80 days.

(21) Appl. No.: 14/602,370

(22) Filed: Jan. 22, 2015

(65) Prior Publication Data
US 2016/0216224 A1 Jul. 28, 2016

(51) Int. Cl.
G01N 27/00 (2006.01)
G01N 27/22 (2006.01)
G01N 27/24 (2006.01)

(52) U.S. Cl.
CPC ........... *G01N 27/221* (2013.01); *G01N 27/24* (2013.01)

(58) Field of Classification Search
CPC .... G01N 27/221; G01N 27/02; G01N 27/228; G01N 27/22; G01N 2033/0095; G01R 27/2605; G06F 3/044; G01D 5/241; G01D 5/2417; G01D 5/2405
See application file for complete search history.

(56) References Cited

U.S. PATENT DOCUMENTS

| 3,243,701 A | | 3/1966 | Strand | |
|---|---|---|---|---|
| 3,715,667 A | * | 2/1973 | Nicolson | G01N 22/02 324/632 |
| 5,309,110 A | * | 5/1994 | O'Neill | G01R 27/2641 324/650 |

(Continued)

*Primary Examiner* — Julian Huffman
*Assistant Examiner* — Michael Konczal
(74) *Attorney, Agent, or Firm* — Warner Norcross & Judd LLP

(57) ABSTRACT

A system and a method for characterizing a dielectric material are provided. The system and method generally include applying an excitation signal to electrodes on opposing sides of the dielectric material to evaluate a property of the dielectric material. The method can further include measuring the capacitive impedance across the dielectric material, and determining a variation in the capacitive impedance with respect to either or both of a time domain and a frequency domain. The measured property can include pore size and surface imperfections. The method can still further include modifying a processing parameter as the dielectric material is formed in response to the detected variations in the capacitive impedance, which can correspond to a non-uniformity in the dielectric material.

15 Claims, 10 Drawing Sheets

(56) References Cited

U.S. PATENT DOCUMENTS

| | | | | |
|---|---|---|---|---|
| 6,229,317 B1* | 5/2001 | Barchuk | ................ | G07D 7/026 |
| | | | | 324/658 |
| 8,890,553 B2* | 11/2014 | Furuta | .................... | G01N 27/02 |
| | | | | 324/525 |
| 2003/0094032 A1* | 5/2003 | Baklanov | ............... | G01N 15/08 |
| | | | | 73/38 |
| 2003/0224544 A1* | 12/2003 | Prisco | .................. | G01N 15/088 |
| | | | | 438/16 |
| 2006/0220498 A1* | 10/2006 | Kremer | .................. | G01M 3/40 |
| | | | | 310/338 |
| 2013/0259505 A1* | 10/2013 | Zaretsky | ............ | G03G 15/0194 |
| | | | | 399/66 |

* cited by examiner

CHARACTERIZATION OF DIELECTRIC MATERIALS

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in the invention.

FIELD OF THE INVENTION

The present invention relates to systems and methods for characterizing materials, and in particular, dielectric materials.

BACKGROUND OF THE INVENTION

Dielectric materials are characterized by a low electrical conductivity and an ability to become polarized in an applied electric field. Dielectric materials are often incorporated into a variety of products, for example capacitors and batteries, specifically because of their dielectric properties. There are also many products that contain dielectric materials that are selected for reasons unrelated to their dielectric properties. For example, oxidation inhibiting coatings and non-woven fabrics are dielectrics, but are often selected for reasons unrelated to their dielectric properties.

Many such dielectric materials are processed in large quantities using continuous manufacturing. Continuous manufacturing can include the roll-processing of dielectric sheets or the continuous application of dielectric coatings or laminates on a moving substrate. During manufacture, however, variations in the dielectric material may occur that affect its electrical or physical properties in ways that impact the quality of the finished product. In some cases, the variations in electrical or physical properties become severe enough that the end product is unusable and must be scrapped after substantial investments in time and material.

Accordingly, there remains a need for a system and a method that can detect variations in dielectric materials, where the variations are sometimes visually undetectable. In particular, there remains a need for a system and a method that can automatically detect variations in the continuous manufacture of dielectric substrates, coatings, and laminates to reduce waste materials and increase the quality of the finished product.

SUMMARY OF THE INVENTION

A system and a method for characterizing a dielectric material are provided. The system and method generally include applying an excitation signal to electrodes on opposing sides of the dielectric material to evaluate a property of the dielectric material. The method can include measuring a current or voltage at the electrodes, optionally in conjunction with the manufacture of the dielectric material.

In one embodiment, a method for evaluating a dielectric material is provided. The method includes providing first and second electrodes and a dielectric material therebetween, applying an excitation signal to at least one of the first and second electrodes to generate an electric field across the dielectric material, measuring the output of the first or second electrode, evaluating a property of the dielectric material based on the measured electrode output with respect to either of both of a time domain and a frequency domain, and adjusting one or more processing parameters if the dielectric material is not within desired manufacturing tolerances. The excitation signal can include a DC waveform or an AC waveform. For example, the excitation signal can include a complex AC waveform having a plurality of component frequencies. Gradual changes in the output of the first or second electrode can indicate a degradation in the material qualities of the dielectric material, including for example pore size, uniformity of material composition, surface imperfections, and sub-surface imperfections. Processing parameters can be altered in real time to avoid interruptions in the production run or the delivery of non-satisfactory dielectrics.

In another embodiment, a system for evaluating a dielectric material is provided. The system includes a first electrode on a first side of the dielectric material and a second electrode on a second side of the dielectric material. The first electrode and the second electrode are capacitively coupled to each other through the dielectric material. The system further includes a waveform generator coupled to the first or second electrode and a measurement circuit coupled to the first or second electrode. The waveform generator is adapted to apply an excitation signal to the first or second electrode, and the measurement circuit is adapted to measure the resulting current or voltage at the first or second electrode. The current or voltage is measured at multiple locations of the dielectric material to evaluate a property of the dielectric material. The first and second electrodes are optionally stationary with respect to a moveable dielectric material. In other embodiments, the first and second electrodes are moveable with respect to a stationary dielectric material. In still other embodiments, one electrode is stationary and the other electrode is moveable. In still other embodiments, the first and second electrodes are stationary and the dielectric material is stationary. The electrodes can extend across the width of the dielectric material, and can alternatively encompass less than the entire width of the dielectric material for localized measurements.

In still another embodiment, a method for evaluating a dielectric substrate is provided. The method includes generating an electric field across the thickness of the dielectric substrate at a plurality of locations along the length of the dielectric substrate, measuring the capacitive impedance across the dielectric substrate at the plurality of locations, and determining a variation in the capacitive impedance across the dielectric substrate to evaluate a property of the dielectric material. Determining a variation in the capacitive impedance can be performed with respect to either or both of a time domain and a frequency domain. The measured property can include pore size, material make-up, and surface imperfections. The method can further include moving the dielectric substrate with respect to first and second electrodes, or moving the first and second electrodes with respect to the dielectric substrate. The method can still further include modifying a processing parameter as the dielectric substrate is formed in response to the detected variations in the capacitive impedance.

The system and method can be used to detect a non-uniformity in the lengthwise and widthwise directions during the continuous manufacture of a dielectric material, even when the non-uniformity is visually undetectable. For example, a perturbation in the electrical output of the first or second electrodes can indicate a growing non-uniformity of one or more properties of the dielectric material. Further by example, the dielectric material can be determined to be drifting out of specification. The perturbation can prompt an investigation of the manufacturing process and a modification of one or more processing parameters to return to uniformity in the dielectric material.

The system and method are equally well suited for a range of other applications. For example, the system and method can determine whether a previously manufactured dielectric material or a previously applied dielectric coating is suitable for use. Example materials and coatings can include a pre-manufactured separator for a battery, a pre-manufactured separator for a fuel cell, or a pre-applied coating for a substrate. The system and method can be used to identify potential defects that might otherwise escape detection, even after the manufacture or application of the dielectric material or coating.

These and other features and advantages of the present invention will become apparent from the following description of the invention, when viewed in accordance with the accompanying drawings and appended claims.

DETAILED DESCRIPTION OF THE CURRENT EMBODIMENTS

The embodiments as contemplated and disclosed herein include a system and a method for characterizing a dielectric material. The system and method generally include measuring the capacitive impedance across the dielectric material to evaluate physical or electrical properties of the dielectric material that might otherwise escape detection. The evaluation can occur in conjunction with the manufacture or application of the dielectric material in some embodiments, while in other embodiments the evaluation can occur apart from the manufacture or application of the dielectric material.

I. Overview

To aid in the discussion of the system and method of the current embodiments, the present application includes the following overview. When a dielectric material is placed between two electrodes, a capacitor is formed, whose impedance $|Z_c|$ at any given frequency, f, is given by equation (1) below:

$$|Z_c|=1/(2\cdot\pi\cdot f\cdot C) \tag{1}$$

At high frequencies the capacitor can exhibit a low impedance, while at low frequencies the capacitor can exhibit a high impedance. The capacitance, C, represented by two parallel plate electrodes with an effective area, A, separated by a dielectric of thickness, d, having a dielectric constant, $\in$, is given by equation (2) below:

$$C=\in \cdot A/d \tag{2}$$

The impedance $|Z_c|$ is therefore inversely proportional to the dielectric constant $\in$.

When a time-varying or AC voltage, v, is applied across the capacitor, a current, i, is generated according to equations (3) and (4) below:

$$i=v/|Z_c| \tag{3}$$

$$i=(v\cdot 2\cdot\pi\cdot f\cdot \in \cdot A)/d \tag{4}$$

The current, i, is directly proportional to the dielectric constant, $\in$. Similarly, an alternating current, i, when applied to the capacitor electrodes, can generate a voltage across the electrodes according to equations (5) and (6) below:

$$v=i\cdot|Z_c| \tag{5}$$

$$v=(i\cdot d)/(2\cdot\pi\cdot f\cdot \in \cdot A) \tag{6}$$

In practice, the dielectric constant, $\in$, may change as a result of physical changes to the dielectric material. For example, the dielectric constant, $\in$, may change as a result of an increase in the porosity or surface imperfections, resulting in a new dielectric constant, and consequently a new capacitive impedance. By monitoring for a change in the dielectric constant or a change in the capacitive impedance, the onset of defects can be detected, optionally in advance of existing detection techniques. For example, an AC or DC voltage can be applied and the resulting current can be monitored with the objective of detecting electrical signatures that are representative of the material properties of interest. Also by example, an AC or DC current can be applied and the resulting voltage can be monitored with the objective of detecting electrical signatures that are representative of the material properties of interest.

II. System

Figure 1:
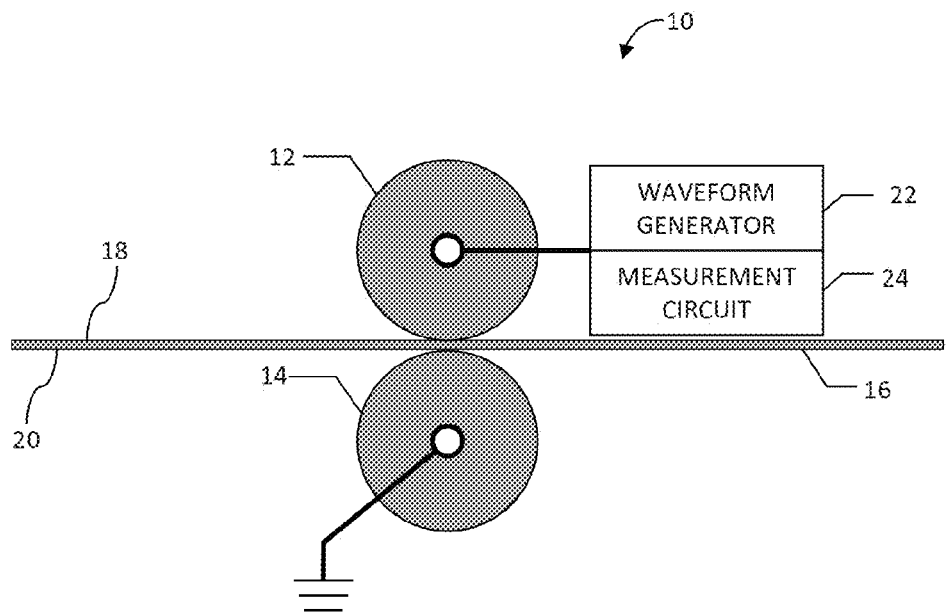
FIG. 1 is a schematic diagram of a system for evaluating a dielectric material in accordance with a first embodiment.

A system for evaluating a dielectric according to the above principles is illustrated in FIG. 1 and generally designated 10. The system includes first and second electrodes 12, 14 positioned on respective first and second sides 18, 20 of a dielectric material 16, such that the first and second electrodes 12, 14 can be capacitively coupled to each other through the dielectric material 16. The electrodes 12, 14 are formed of an electrically conductive material, for example copper, brass, or steel. The electrodes 12, 14 are rollers in the illustrated embodiment, but as discussed below the electrodes 12, 14 can assume other configurations in other embodiments. As alternatively shown in FIG. 2 for example, one or both electrodes 12, 14 can include plates that are positioned opposite each other, being separated by a distance at least equal to the thickness of the dielectric material 16. Example dielectric materials include plastics, carbon fibers, ceramics, glass-ceramics, and oxides of various metals. The dielectric material 16 is depicted as a substrate, but can include other configurations, including for example coatings, laminates, lines, or patterns. Other configurations are suitable in other embodiments as desired.

Figure 4:
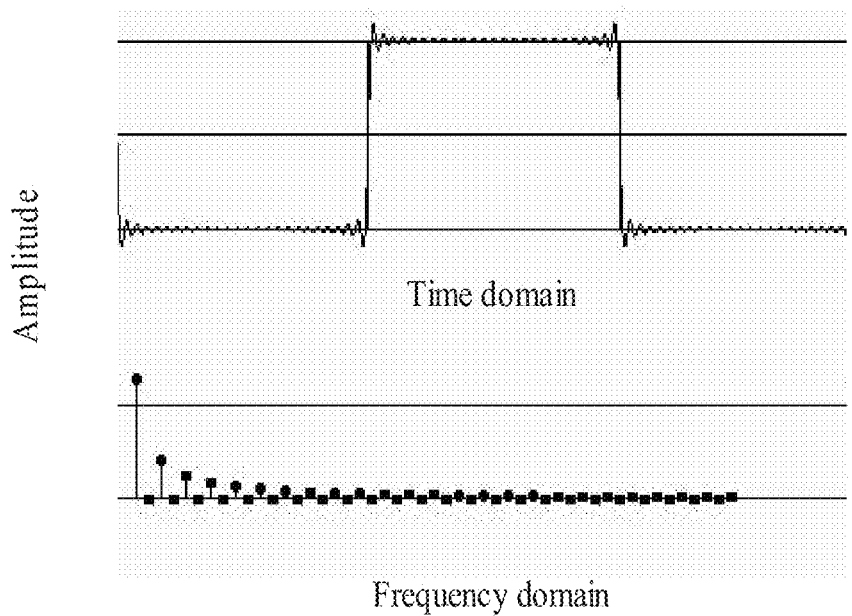
FIG. 4 is a graph illustrating a square waveform as represented in both the time domain and the frequency domain.
Figure 10:
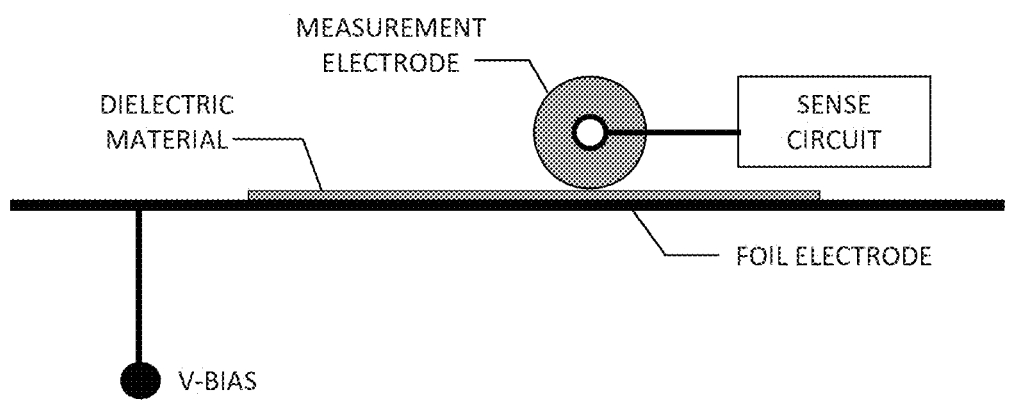
FIG. 10 is a schematic diagram of a system for evaluating a dielectric material in accordance with an example as set forth below.

Referring again to FIG. 1, one of the first and second electrodes 12, 14 is electrically coupled to a waveform generator 22 and a measurement circuit 24. In other embodiments, the waveform generator 22 is coupled to one of the first and second electrodes 12, 14 and the measurement circuit 24 is coupled to the other of the first and second electrodes 12, 14. This configuration is generally illustrated in FIG. 10, for example. The waveform generator 22 is adapted to apply an excitation signal (at a known voltage or a known current) to the first electrode 12, and the measurement circuit 24 is adapted to measure the current or voltage at the first electrode 12 relative to the second electrode 14, which is illustrated as tied to ground. For example, the waveform generator 22 can include a DC power supply, where the waveform that is measured is the variation in current or voltage which arises from the changes in the dielectric constant of the dielectric material 16. Also by example, the waveform generator 22 can include a simple harmonic oscillator that produces an excitation signal having a fixed frequency. Further by example, the waveform generator 22 can include a complex waveform generator that produces a complex excitation signal. The complex excitation signal can be represented as an infinite series of pure sinusoidal waveforms at different frequencies through Fourier decomposition. For example, a square wave can be represented by an infinite series in which the fundamental frequency, $f_1$, exists at unity amplitude, the third harmonic, $f_3$, exists at ⅓ amplitude, and the fifth harmonic, $f_5$, exists at ⅕ amplitude ad infinitum as shown in FIG. 4. In embodiments where a complex excitation signal is generated, the dielectric constant, $\in$, can be measured at multiple dominant frequencies.

Figure 3:
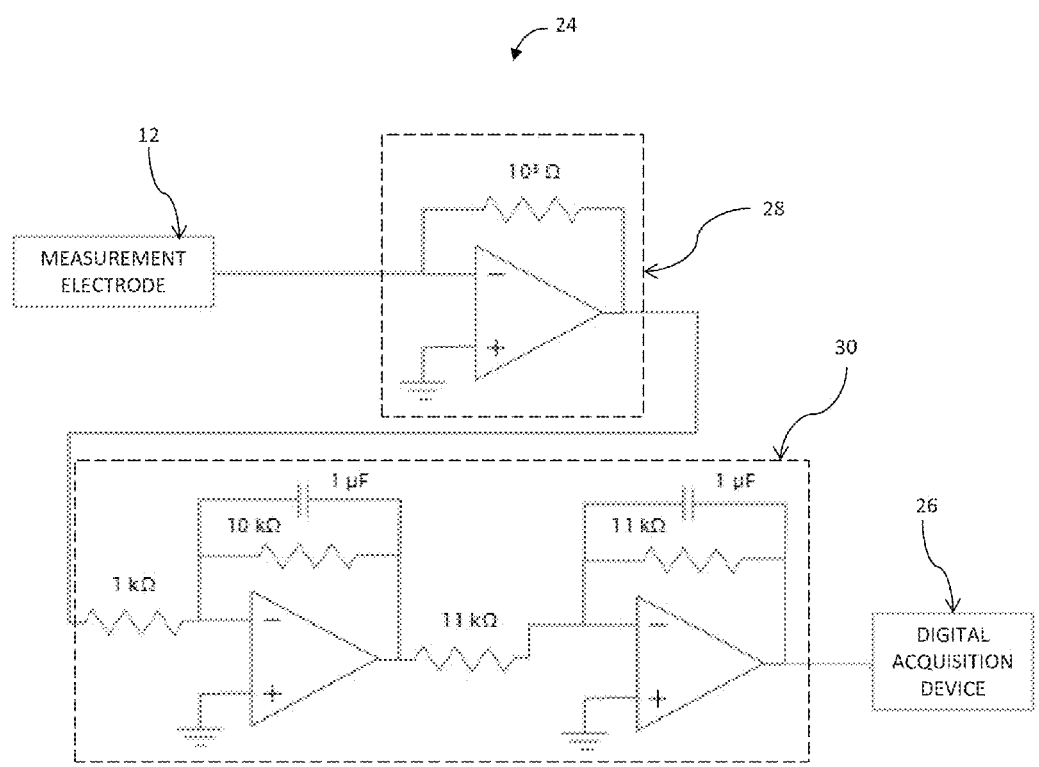
FIG. 3 is a circuit diagram of an exemplary measurement circuit as depicted in FIGS. 1-2.

Referring to FIG. 3, a measurement circuit 24 is illustrated. The measurement circuit 24 is generally adapted to measure the instantaneous current or the instantaneous voltage at the measurement electrode (which may be the same or different than the excitation electrode) for output to a digital acquisition device 26. While shown as being analog, the measurement circuit 24 can alternatively include digital circuitry for measuring the instantaneous current or the instantaneous voltage. In the illustrated embodiment, the current (or voltage) at the measurement electrode is output to a high gain converter 28, followed by a two stage low-pass filter 30. The low pass filter 30 can mitigate the effects of electromagnetic interference, including for example interference due to 60 Hz electric fields. The filter can additionally or alternatively include a high pass filter, a low pass filter, a band pass filter, or a band reject filter.

A number of additional techniques exist for limiting electromagnetic interference. For example, the measurement circuit 24 can include electromagnetic shielding in place of, or in addition to, the filter 30. The electromagnetic shielding can be selected to limit interference from nearby power supplies operating at 60 Hz. Also by example, the measurement circuit 24 can include a phase lock loop that locks the phase of the measurement electrode with the phase of the excitation signal, discarding signals that are not substantially in phase with the excitation signal. In this embodiment, 60 Hz signals can be processed by the digital acquisition device 26 while limiting interference from nearby power supplies operating at 60 Hz. Additional filtering methods can be used in other embodiments as desired, including filtering methods performed in digital logic.

Figure 5:
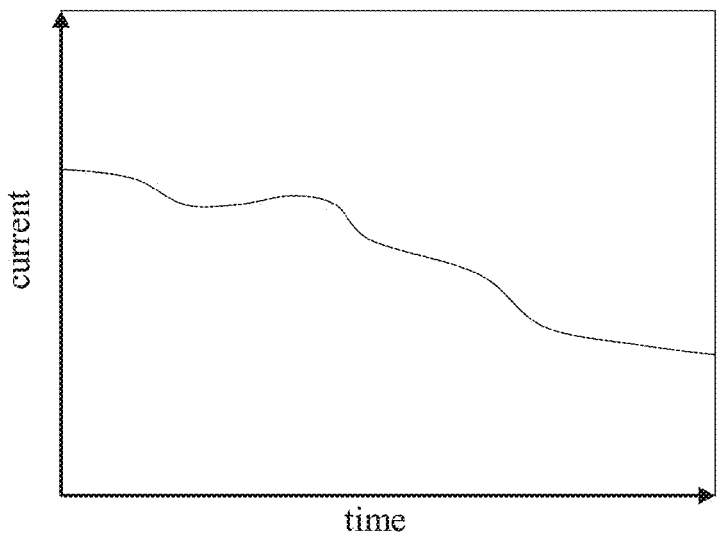
FIG. 5 is a graph illustrating a current waveform having a decreasing amplitude with respect to a time domain.
Figure 6:
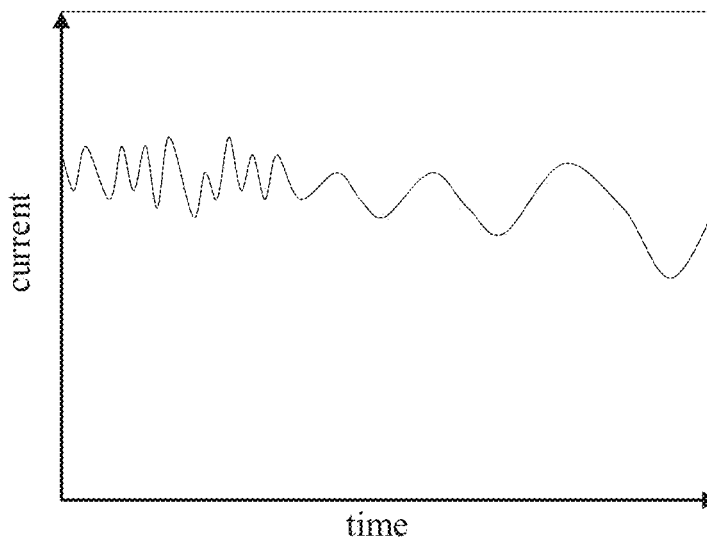
FIG. 6 is a graph illustrating a current waveform having a decreasing frequency with respect to a time domain.

Referring now to FIGS. 5-6, the output of the measurement circuit 24 is depicted over time for two dielectric samples. The first dielectric sample demonstrated a gradual decrease in amplitude over time, while the second dielectric sample demonstrated a gradual decrease in frequency over time. The gradual decrease in amplitude in FIG. 5 and the gradual decrease in frequency in FIG. 6 can be correlated to a change in a manufacturing parameter, for example a change in the porosity of the dielectric material. The somewhat gradual change in both examples can indicate that a process parameter in the manufacture of the dielectric material is drifting out of specification and should then be corrected.

Figure 7:
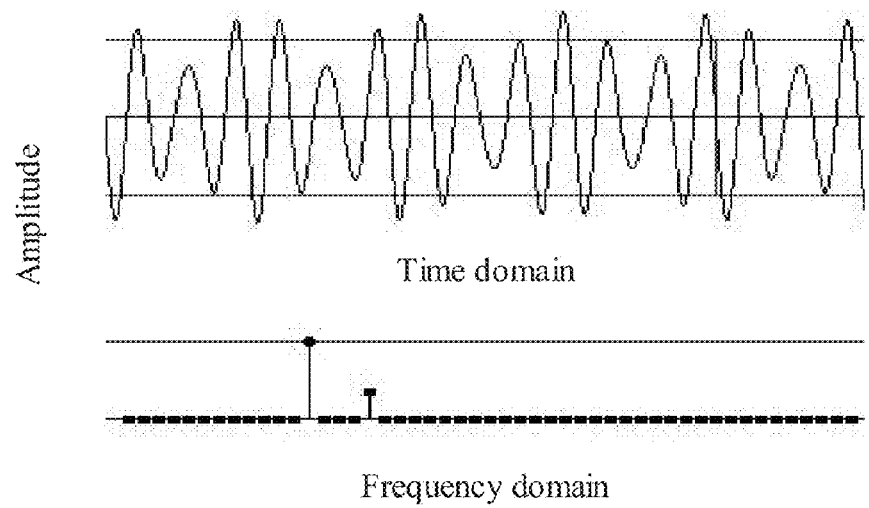
FIG. 7 is a graph illustrating an electric signature of a dielectric material with two frequency components.
Figure 8:
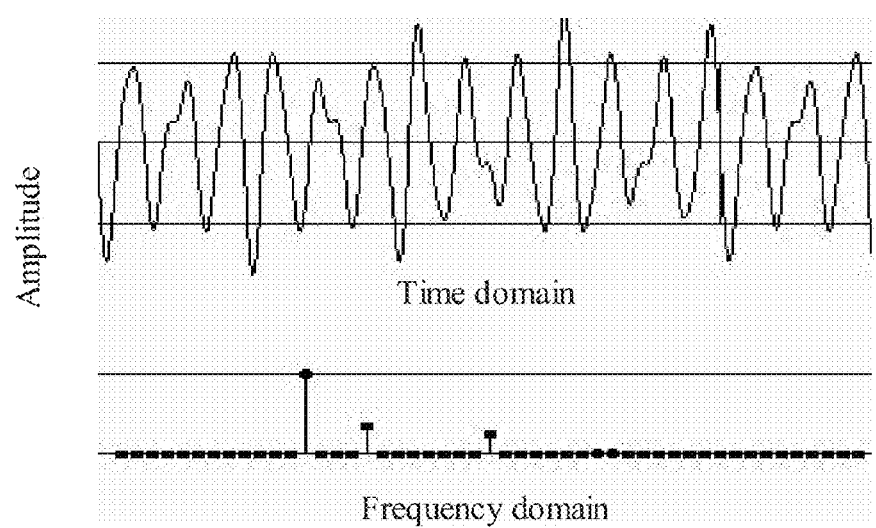
FIG. 8 is a graph illustrating an electric signature of a dielectric material with three frequency components.

The output of the measurement circuit 24 can additionally be analyzed with respect to a frequency domain. FIGS. 7-8 depict two waveforms (current or voltage) with a time domain and a frequency domain. While the waveforms appear similar in the time domain, the waveforms are visibly different in the frequency domain. In particular, the waveform of FIG. 7 includes two dominant frequencies, while the waveform of FIG. 8 includes a third dominant frequency. In practice, FIG. 7 may represent an electric signature that is characteristic of normal manufacturing parameters, while FIG. 8 may represent an electric signature in which a third dominant frequency is indicative of a problematic manufacturing parameter that requires investigation.

Various modifications can be made to the system 10 discussed above. For example, in some embodiments the dielectric material 16 can exist as printed lines on a substrate. In these embodiments, the system 10 can identify the printed dielectric lines by monitoring the current or voltage as the substrate moves with respect to the electrodes 12, 14. The proximity of the printed dielectric lines can cause an increase in current or voltage at the measurement electrode, followed by a decrease in current or voltage at the measurement electrode. The period between current or voltage "peaks" (local maxima) at the measurement electrode can be monitored by the digital acquisition device 26 for variations that might indicate the spacing between adjacent dielectric lines is incorrect.

The electrodes 12, 14 can extend along the entire width of the dielectric material 16, or can extend along less than the entire width of the dielectric material 16. For example, electrodes 12, 14 that extend along the entire width of the dielectric material can detect dielectric variations (non-uniformity) in the lengthwise direction (i.e., in the direction of travel) but are generally prevented from detecting dielectric variations in the widthwise direction (i.e., transverse to the direction of travel). To detect dielectric variations (non-uniformity) in the widthwise direction, the electrodes 12, 14 can be segmented into smaller units that are spaced apart from each other by use of an insulator or air gap. For example, the rollers 12, 14 depicted in FIG. 1 can be separated into four even width top rollers and four even width bottom rollers to detect dielectric variations in both the lengthwise directions and the widthwise directions. Each electrode pair can receive substantially the same excitation signal, and can output to a corresponding measurement circuit before being processed by a digital acquisition device 26. By comparing the output among electrode pairs, the digital acquisition device 26 can identify widthwise variations that might otherwise escape detection with only a single pair of horizontal roller electrodes 12, 14.

The system 10 can additionally be configured to test for dielectric breakdown in the dielectric material. For example, the waveform generator 22 can provide an excitation signal whose power gradually increases until dielectric breakdown is detected by the measurement circuit, after which time the excitation signal is terminated or lowered to prevent damage to the dielectric material 15.

III. Method

Figure 9:
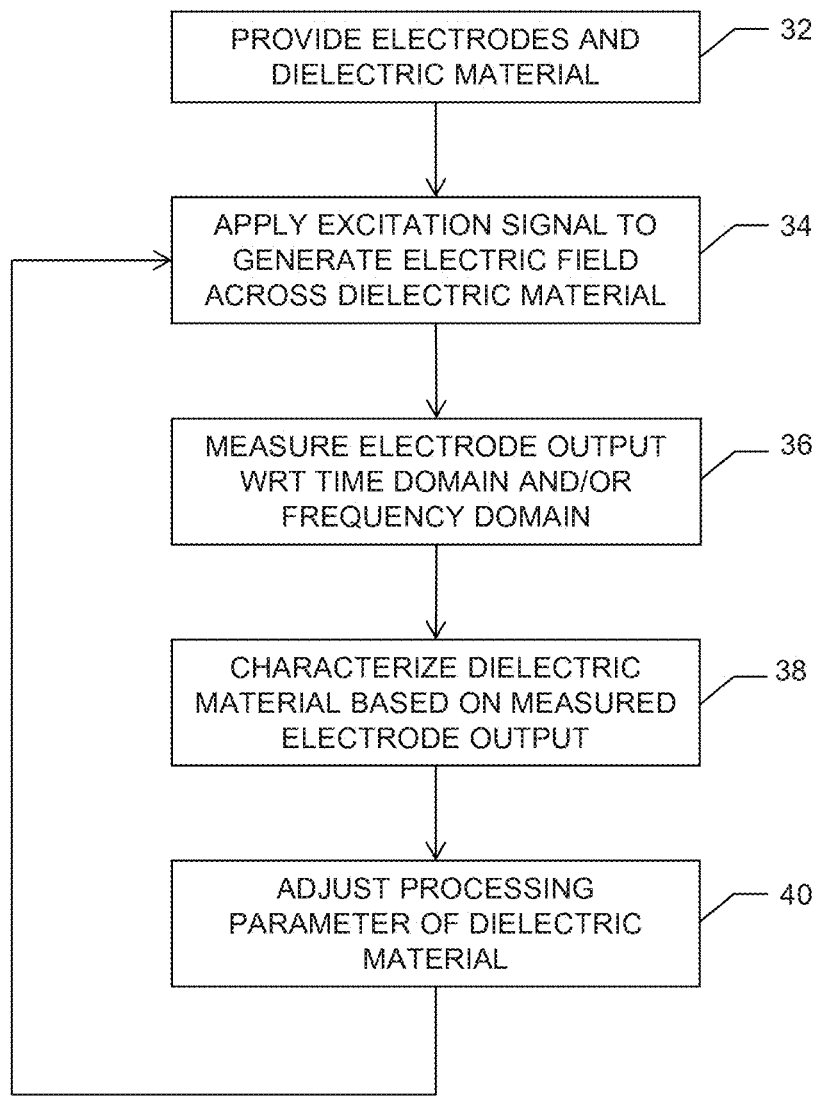
FIG. 9 is a flow chart for a method of evaluating a dielectric material in accordance with a current embodiment.

Referring now to FIG. 9, a flow chart illustrating a method for evaluating a dielectric material is provided. In general terms, the method according to one embodiment includes: a) providing first and second electrodes and a dielectric material therebetween; b) applying an excitation signal to at least one of the first and second electrodes to generate an electric field across the dielectric material; c) measuring the output of the first or second electrode; d) characterizing the dielectric material based on the measured electrode output with respect to either of both of a time domain and a frequency domain; and e) adjusting one or more processing parameters if the dielectric material is not measuring within desired manufacturing tolerances.

Figure 2:
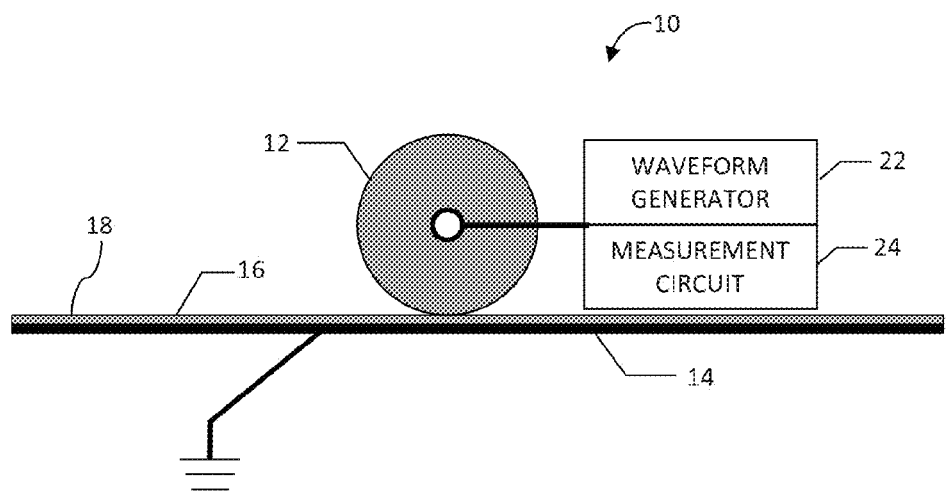
FIG. 2 is a schematic diagram of a system for evaluating a dielectric material in accordance with a second embodiment.

Providing first and second electrodes and a dielectric material is depicted as step 32 in FIG. 9. This step generally includes providing a first electrode on a first side of the dielectric material and providing a second electrode on a second side of the dielectric material. Where the dielectric material is a substrate, for example a continuous substrate as illustrated in FIGS. 1-2, the first side of the dielectric material is a first major surface and the second side of the dielectric material is a second major surface. Example dielectric materials include plastics, carbon fibers, ceramics, glass-ceramics, and oxides of various metals. Alternatively, the dielectric material can include a coating or a laminate. The dielectric materials are generally dimensionally stable members, optionally defining a thickness and a length. The electrodes are separated by a distance equal to or greater than the thickness of the dielectric material, are movable or stationary with respect to the dielectric material, and engage or are spaced apart from the dielectric material.

Applying an excitation signal to at least one of the first and second electrodes to generate an electric field across the dielectric material is depicted as step 34 in FIG. 9. As used herein, an "excitation signal" includes a current or a voltage, the current or voltage being substantially constant or being time-varying. For example, an excitation signal can include DC current or voltage or an AC current or voltage. If an AC current or voltage is applied to an electrode, the excitation signal can include a sinusoidal waveform or a complex waveform having multiple component waveforms. The excitation signal is generally applied by a waveform generator, depicted as item 22 in FIGS. 1-2. The waveform generator can be any conventional signal generator adapted to provide a known output, including for example a simple harmonic oscillator.

Measuring the electrode output is depicted as step 36 in FIG. 9. This step generally includes sampling the current or voltage at one or both of the electrodes. The current or voltage can then be analyzed with respect to a time domain, analyzed with respect to a frequency domain, or analyzed with respect to both of a time domain and a frequency domain. To measure the dielectric constant, $\in$, as a function of frequency, f, the dielectric constant can be calculated using equation (7) below with knowledge of the excitation signal (i or v) and the measured electrode output (v or i):

$$\in = (i \cdot d)/(v \cdot 2 \cdot \pi \cdot f \cdot A) \quad (7)$$

For example, a time domain analysis may indicate that, over time, the dielectric constant decreased or the capacitive impedance decreased to less than acceptable levels for a given product run. This can be attributable to changes in the porosity, thickness uniformity, compositional homogeneity, or structural homogeneity, for example. In other embodiments the electrical signature can be measured and monitored over time. As used herein, an "electrical signature" includes one or more characteristics of the measurement electrode output with respect to a domain, for example a time domain or a frequency domain. The characteristics can include a dominant frequency (most easily viewed with respect to a frequency domain) or an amplitude (most easily viewed with respect to a time domain). Other characteristics of the electrical signature can also be measured. In addition, multiple measurements can be performed along the length of the dielectric material. This can increase the likelihood that gradual variations in the electrical signature will be captured by the method of the present embodiment, for example throughout a production run.

Characterizing the dielectric material is depicted as step 38 in FIG. 9. This step generally includes determining whether the measured dielectric constant, $\in$, the measured capactively impedance, $|Z_c|$, or the electrical signature is within acceptable levels. If an expected value is known, this step can include the comparison of the measured value with the expected value. Alternatively, this step can include detecting variations in the measured value over time, and determining if these variations are outside of acceptable levels or are within acceptable levels but trending toward unacceptable levels. For example, the emergence of a new dominant frequency as shown in FIG. 8 can indicate the electrical signature is outside of acceptable levels, or the amplitude of the new dominant frequency is such that the electrical signature is merely approaching unacceptable levels. In this regard, the method of the present invention provides for the non-invasive evaluation and characterization (e.g., as conforming or non-conforming) of a dielectric material, optionally as part of an ongoing production run.

Adjusting one or more processing parameters of the dielectric material is depicted as step 40 in FIG. 9. This step generally includes causing incremental modifications to one or more dielectric processing parameters in response to step 38 above. For example, the following processing parameters may be modified (or caused to be modified) in the manufacture of the dielectric material: the ratio of constituent ingredients; the mixing parameters; the heating profile; and the cooling profile. Other processing parameters may be modified in other embodiments. In addition, the dielectric constant or electrical signature can be continuously monitored as the processing parameters are modified. In this respect, control of the processing parameters includes a negative feedback loop where the actual value is the measured dielectric constant, the measured capacitive impedance, or the measured electrical signature, and the reference value is an expected dielectric constant, an expected capacitive impedance, or an expected electrical signature.

The above method can be utilized in connection with the digital acquisition device 26 of FIG. 3. The digital acquisition device 26 includes an internal processor to execute a series of commands representing one or more method steps schematically depicted in FIG. 9. For example, the digital acquisition device 26 is generally programmed with a series of instructions that, when executed, cause the processor to perform method steps 38 and 40 as described above. The instructions that are performed by the internal processor are generally stored in a computer readable data storage device. The computer readable data storage device can be a portable memory device that is readable by the computer apparatus. Such portable memory devices can include a compact disk, a digital video disk, a flash drive, and any other disk readable by a disk driver embedded or externally connected to a computer, a memory stick, or any other portable storage medium whether now known or hereinafter developed. Alternatively, the machine-readable data storage device can be an embedded component of a computer such as a hard disk or a flash drive of a computer. Together, the computer and machine-readable data storage device can be a stand-alone device or embedded into a machine or a system that uses the instructions for a useful result.

IV. Example

Three dielectric resins were evaluated and compared according to the above method in the following example, which is intended to be non-limiting.

Three dielectric materials were provided: HPX4, HPXF and Celgard. The dielectric materials were available from SABIC Innovative Plastics or Celgard, LLC and are conventionally used as battery separator materials. The dielectric materials exhibited a virtually identical visual appearance, and were placed on a flat foil substrate as shown in FIG. 10. An applied bias voltage of one volt was applied to the foil electrode, and a measurement electrode was rolled across the surface samples (approximately 100 mm) using a computer-controlled translation stage at approximately 2.5 mm/min. The measurement electrode was electrically connected to a measurement circuit, which included a high gain amplifier and a two-stage low pass filter as shown in FIG. 3.

Figure 11:
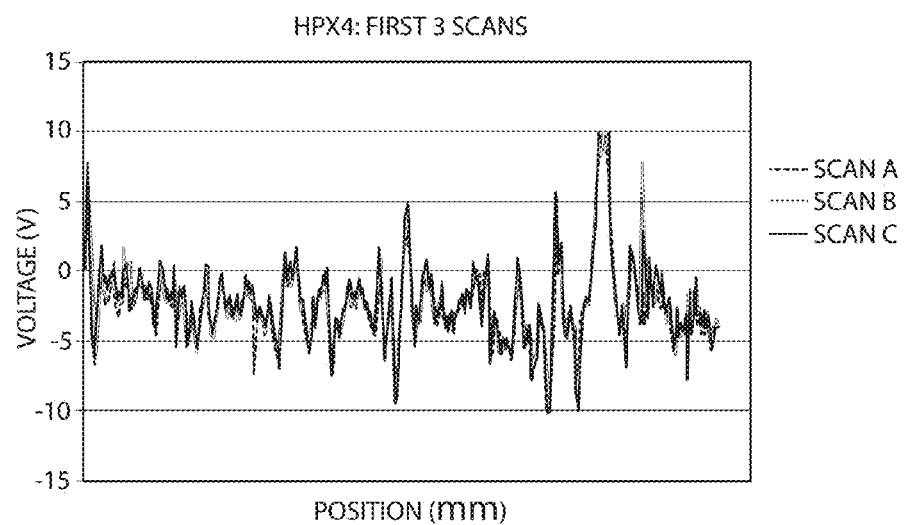
FIG. 11 is a graph illustrating multiple scans of a dielectric material for validating the repeatability of the system of FIG. 10.
Figure 12:
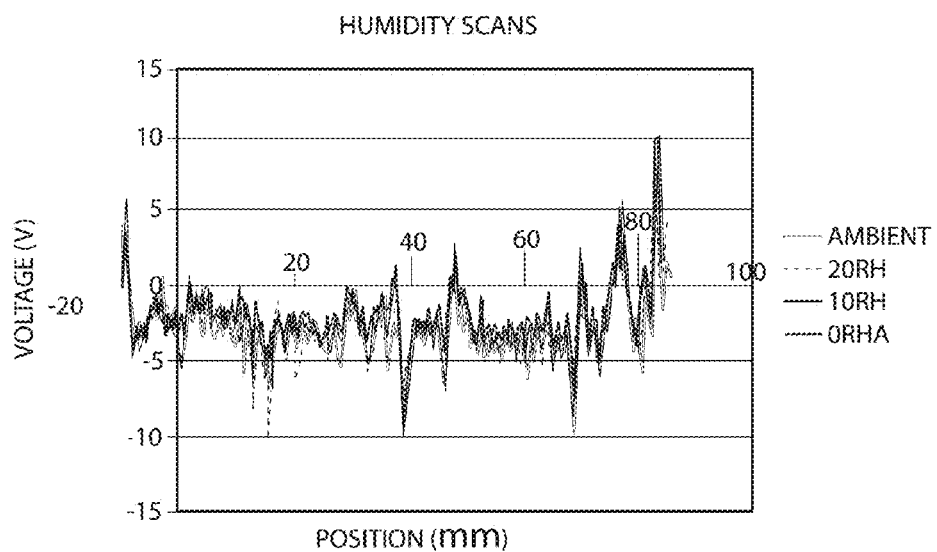
FIG. 12 is a graph illustrating multiple scans of a dielectric material for evaluating the effects of humidity on the system of FIG. 10.
Figure 13:
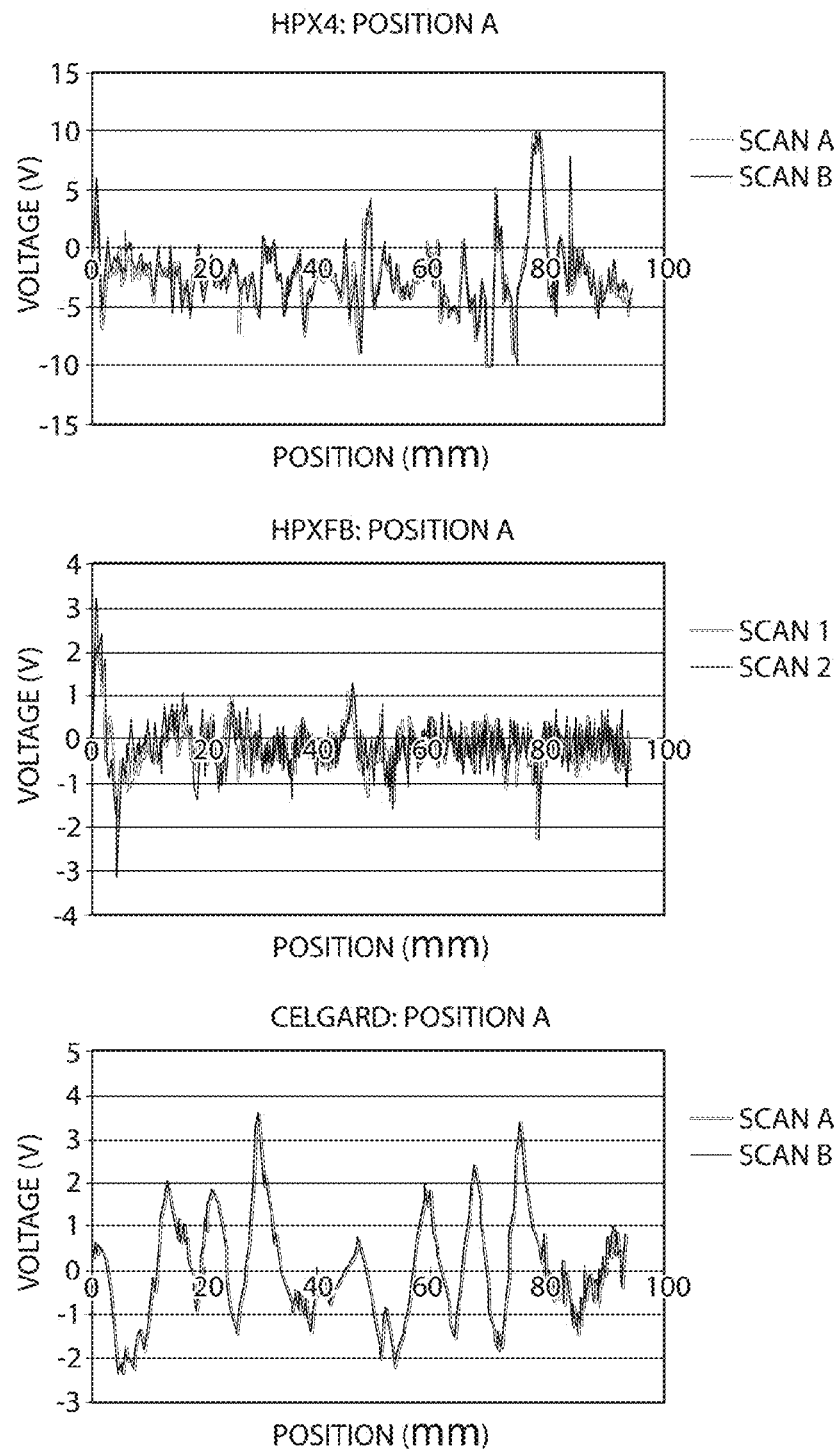
FIG. 13 includes graphs illustrating different electronic signatures for different dielectric samples when measured according to the system of FIG. 10.
Figure 14:
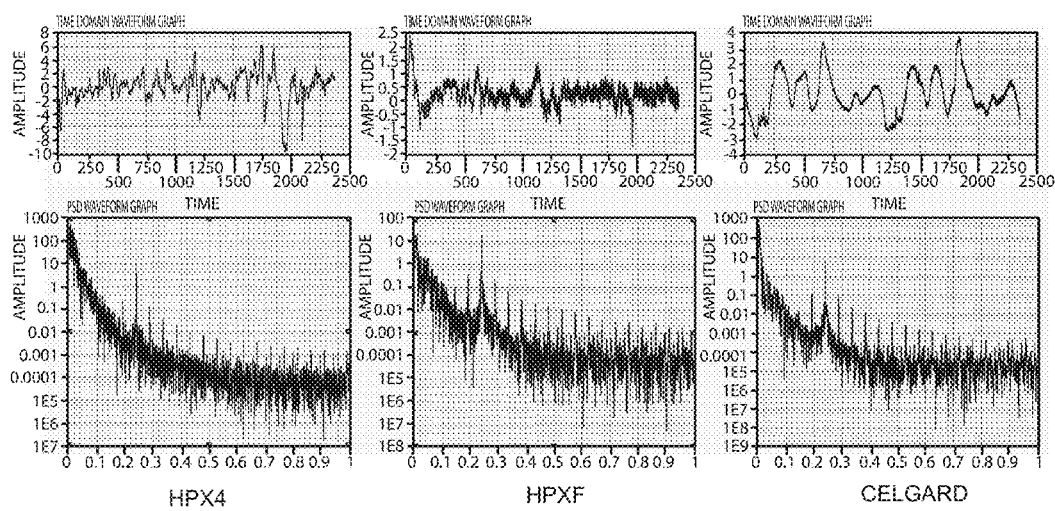
FIG. 14 includes time domain graphs and frequency domain graphs for different dielectric samples when measured according to the system of FIG. 10.

The system was initially evaluated to verify repeatability. The HPX4 sample was scanned in three consecutive tests and the waveforms for each test were virtually identical, as shown in FIG. 11. The system was then evaluated to determine sensitivity to humidity. The HPX4 was scanned within a humidistatic chamber at 0%, 10%, 20% and ambient (~40%) humidity with one hour between scans to allow the humidity to reach equilibrium. The waveforms were nearly identical among the four scans as shown in FIG. 12. Subsequent scans were performed to evaluate the signature difference between the dielectric materials. As shown in FIG. 13, the Celgard sample was dominated by low frequencies, the HPXF sample was dominated by high frequencies, and the HPX4 sample was in between. The power spectral densities (PSDs) for these materials are shown in FIG. 14, including both time domain and frequency domain comparisons. As also shown in FIG. 14, the three visually similar materials demonstrated three very distinct electrical signatures with regard to the nature of the time domain waveforms and the frequency components in their signatures. The distinct electrical signatures can be due to a difference in porosity, thickness or other property. By extension, the present example can be modified to determine uniformity of a dielectric material during its manufacture. For example, the electrical signature of the dielectric material can be evaluated over time to identify perturbations indicating non-uniformity in the lengthwise and/or widthwise directions. The perturbation can prompt an investigation into the manufacturing process and a modification of one or more processing parameters in order to return to uniformity in the dielectric material.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements by ordinal terms, for example "first," "second," and "third," are used for clarity, and are not to be construed as limiting the order in which the claim elements appear. Any reference to claim elements in the singular, for example, using the articles "a," "an," "the" or "said," is not to be construed as limiting the element to the singular.

The invention claimed is:

1. A method for evaluating a dielectric material comprising:
    providing a dielectric material including a first major surface, a second major surface, and a thickness therebetween;
    providing a first electrode adjacent the first major surface and a second electrode adjacent the second major surface, wherein the first and second electrodes and the dielectric material are moveable relative to each other in a lengthwise direction of the dielectric material;
    applying an excitation signal to at least one of the first and second electrodes to generate an electric field across the dielectric material, wherein the excitation signal includes an alternating current waveform having a plurality of component frequencies;
    measuring the electrical signature of the dielectric material by sampling the current or voltage from at least one of the first and second electrodes; and
    comparing the measured electrical signature against an expected electrical signature to evaluate, based on the comparison, a property of the dielectric material over at least a portion of the length of the dielectric material, wherein the property of the dielectric material includes pore size.

2. The method according to claim 1 wherein the electrical signature includes the amplitude of the sampled current or voltage over time.

3. The method according to claim 1 wherein the electrical signature includes the frequency of the sampled current or voltage over time.

4. The method according to claim 1 wherein the electrical signature includes the dominant frequencies of the sampled current or voltage.

5. The method according to claim 1 wherein measuring the electrical signature is performed at the plurality of component frequencies.

6. The method according to claim 1 wherein providing the dielectric material includes manufacturing the dielectric material in accordance with a processing parameter, the method further including adjusting the processing parameter for the manufacture of a further dielectric material in view of the comparison of the measured electrical signature against the expected electrical signature.

7. A system for characterizing a dielectric material comprising:
   a first electrode on a first side of the dielectric material and a second electrode on a second side of the dielectric material, wherein the dielectric material and at least one of the first and second electrodes are moveable relative to each other in a lengthwise direction of the dielectric material, the first electrode being capacitively coupled to the second electrode through the dielectric material to define a capacitive coupling;
   a waveform generator adapted to provide an excitation signal to at least one of the first electrode and the second electrode of the capacitive coupling, wherein the excitation signal includes an alternating current waveform having a plurality of component frequencies and wherein the excitation signal causes a current or a voltage at the capacitive coupling; and
   a measurement circuit electrically coupled to at least one of the first electrode and the second electrode, the measurement circuit being adapted to measure the current or the voltage at the capacitive coupling for evaluating a property of the dielectric material over at least a portion of the length of the dielectric material, wherein the property of the dielectric material includes pore size.

8. The system of claim 7 wherein the dielectric material is a continuous roll-formed substrate.

9. The system of claim 8 wherein the first electrode is a roller having a cylindrical outer surface in engagement with the first side of the roll-formed substrate.

10. The system of claim 9 wherein the second electrode is a roller having a cylindrical outer surface in engagement with the second side of the roll-formed substrate.

11. The system of claim 9 wherein the second electrode is a conductive plate having a major surface in engagement with the second side of the roll-formed substrate.

12. A method for evaluating a dielectric substrate comprising:
   providing a dielectric substrate including a first major surface, a second major surface, a thickness therebetween, and a length;
   providing a first electrode adjacent the first major surface and a second electrode adjacent the second major surface, the dielectric material and at least one of the first and second electrodes being moveable relative to each other in a lengthwise direction of the dielectric material;
   generating an electric field across the thickness of the dielectric substrate at a plurality of locations along the length of the dielectric substrate by applying an excitation signal to at least one of the first and second electrodes, wherein the excitation signal includes an alternating current waveform having a plurality of component frequencies;
   measuring the capacitive impedance across the dielectric substrate at the plurality of locations along the length of the dielectric substrate; and
   determining a variation in the capacitive impedance of the dielectric substrate along the length of the dielectric substrate to evaluate, based on the determined variation, a property of the dielectric material over at least a portion of the length of the dielectric material, wherein the property of the dielectric material includes pore size.

13. The method according to claim 12 wherein measuring the capacitive impedance is performed with respect to a time domain.

14. The method according to claim 12 wherein measuring the capacitive impedance is performed with respect to a frequency domain.

15. The method according to claim 12 wherein determining a variation in the capacitive impedance is based on a change in capacitive impedance over time.

* * * * *